(12) United States Patent
Rizun

(10) Patent No.: US 10,967,004 B2
(45) Date of Patent: Apr. 6, 2021

(54) MINERAL PITCH RESIN PRODUCTS AND METHODS OF MANUFACTURING THE PRODUCTS

(71) Applicant: Nodari Rizun, San Diego, CA (US)

(72) Inventor: Nodari Rizun, San Diego, CA (US)

(*) Notice: Subject to any disclaimer, the term of this patent is extended or adjusted under 35 U.S.C. 154(b) by 0 days.

(21) Appl. No.: 16/167,200

(22) Filed: Oct. 22, 2018

(65) Prior Publication Data

US 2019/0336527 A1    Nov. 7, 2019

Related U.S. Application Data

(60) Provisional application No. 62/667,327, filed on May 4, 2018.

(51) Int. Cl.
*A61K 35/04* (2006.01)
*A61K 33/24* (2019.01)
*A61K 33/38* (2006.01)

(52) U.S. Cl.
CPC .............. *A61K 35/04* (2013.01); *A61K 33/24* (2013.01); *A61K 33/38* (2013.01)

(58) Field of Classification Search
CPC ........ A61K 35/04; A61K 33/38; A61K 33/24; A61K 33/35
See application file for complete search history.

(56) References Cited

U.S. PATENT DOCUMENTS

| 3,541,794 A | 11/1970 | Wiliams | |
|---|---|---|---|
| 2013/0280291 A1* | 10/2013 | Rizun | A61K 35/02 424/195.18 |
| 2016/0213713 A1* | 7/2016 | Rizun | A61J 1/05 |

FOREIGN PATENT DOCUMENTS

GB    2314270 B    7/2000

OTHER PUBLICATIONS

International Search Report and Written Opinion dated Jul. 10, 2019 for related International Application No. PCT/US2019/030697, in 9 pages.

* cited by examiner

*Primary Examiner* — Snigdha Maewall
(74) *Attorney, Agent, or Firm* — Procopio, Cory, Hargreaves & Savitch LLP; Lisel M. Ferguson

(57) ABSTRACT

Compositions and methods of mineral pitch resin as a semisolid, solid, and powder comprising a higher than negligible content of at least one of gold, silver and platinum are provided. For example, the product could have a content of above 1 ppm of one or more precious metals. Such mineral pitch resin compositions may be safely consumed orally or topically. Compositions and methods of mineral pitch resin comprising at least one of gold, silver and platinum added during processing to result in a product having a content of above 0.01 ppm of a precious metal is also provided.

16 Claims, 2 Drawing Sheets

MINERAL PITCH RESIN PRODUCTS AND METHODS OF MANUFACTURING THE PRODUCTS

CROSS-REFERENCE TO RELATED APPLICATIONS

This application claims priority to U.S. Provisional Application Ser. No. 62/667,327, filed on May 4, 2018 and titled MINERAL PITCH RESIN PRODUCTS AND METHODS OF MANUFACTURING THE PRODUCTS. This and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

FIELD OF THE INVENTION

The field of the invention is mineral pitch resin as a product in various forms (e.g., semisolid, liquid, solid and powdered) for human consumption, and methods of manufacturing the same. More specifically, the field of the invention is mineral pitch resin products including one or more metals such as gold, silver, or platinum, and methods of manufacturing the same.

SUMMARY OF THE INVENTION

Mineral Pitch resin for human consumption is also known as shilajit, mumie, moomia, salajeet, and so forth. Shilajit is often associated with health benefits, and is orally consumed or topically applied by users in many countries throughout the world. Some of the health benefits associated with shilajit include, among other things, healing of skin wounds, improved circulation, improved stamina, stress relief, improved skin, hair and nails, and increased sexual potency.

Some companies have claimed the availability of "gold" shilajit, creating the perception that their shilajit has a high content of gold. The use of shilajit is largely ayurvedic and not allopathic, and this situation is often exploited by marketers to trick consumers into believing their products have a beneficial element or property they do not in fact have.

The inventor has found that "gold" shilajit marketed by numerous companies in fact had negligible or zero gold content. As metals in their free form in mineral pitch can be highly beneficial, the products and methods described herein are directed towards producing shilajit products with high contents of gold (or silver, platinum or other metal having healing or beneficial properties). As used herein, the term "negligible gold content" refers to a gold content of less than 1 ppm gold content, for example less than 0.01 ppm gold content.

The inventive subject matter provides mineral pitch resin products comprising at least one of gold, platinum and silver. In some aspects, the inventive subject matter provides mineral pitch resin products comprising at least one of gold, platinum and silver present in an amount above 0.01 ppm, above 0.1 ppm, above 1 ppm, above 50 ppm, above 75 ppm, above 100 ppm, above 125 ppm, above 150 ppm, or even higher. The precious metals and products are safe for consumption, may be orally bioavailable, and may be topically applied for treatment or prevention of wounds, wrinkles, or skin imperfections. Additionally, they may increase intelligence and brain function, improve immunity, lead to healthier tissue and bones, and provide several other benefits. Applicant surprisingly discovered that mineral pitch with high gold content will specifically have pronounced beneficial effect on joint health and wellness and mental acuity and balance, while mineral pitch with high silver content will have pronounced beneficial effect on immune health and natural body defenses, and mineral pitch with high platinum content will have pronounced effect on longevity and metabolic processes.

The inventive subject matter also provides methods of producing mineral pitch resin products comprising one or more precious metals in non-negligible amounts, for example in amounts greater than 1 ppm. The inventive subject matter also provides mineral pitch resin products and methods of producing mineral pitch resin products comprising one or more precious metals in an amount above 0.01 ppm where at least some of the precious metals are added during production.

BRIEF DESCRIPTION OF THE FIGURES

The accompanying figures, which are incorporated in and constitute a part of the specification, illustrate embodiments of the invention and, together with the description, serve to explain the objects, advantages, and principles of the invention. In the drawings.

DETAILED DESCRIPTION OF THE INVENTION

Figure 1:
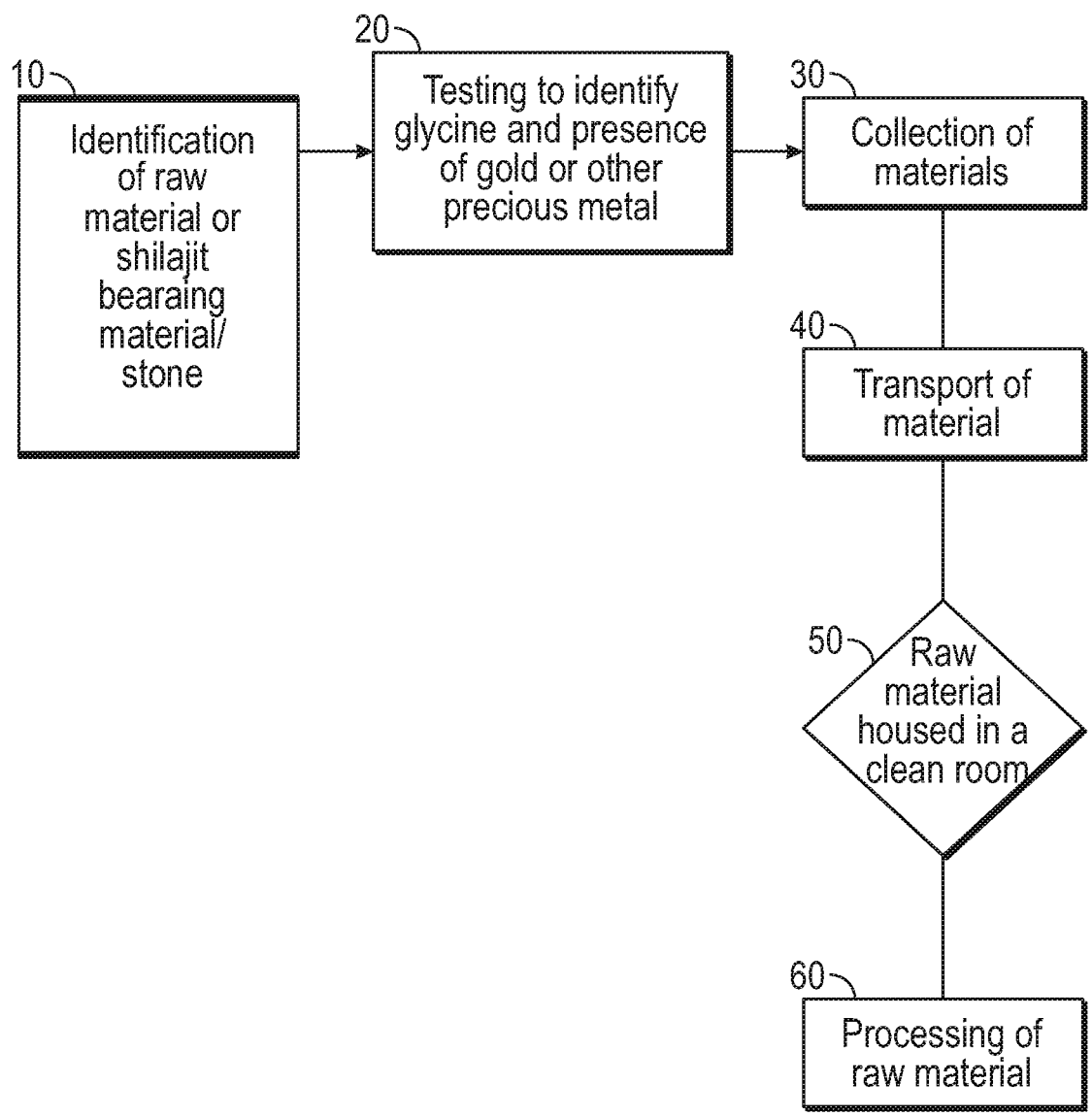
FIG. 1 is a flow diagram which shows the steps in an exemplary method of creating resin for human consumption.

Embodiments described herein are directed to a method for extracting raw mineral pitch resin from naturally found sources and then utilizing a multi-step processing method to manufacture the same so that it is (1) virtually free from harmful contaminants, (2) includes a relatively high content of gold, silver, platinum or other desirable metal, (3) beneficial for joint and skeletal health, and (4) is safe for humans to consume as a healing, tonifying and adaptogenic substance.

First raw material needs to be identified for the resin. The preference is given to locations which are close to at least one of gold, platinum and silver deposits. Such locations are usually situated in the mountains at great distances from cities and polluted areas. Once samples are collected, they may be taken to a laboratory or tested in the field to identify the presence of gold, or platinum, or silver, and the presence of glycine (which indicates that the sample includes shilajit).

The detailed procedure for identifying and processing shilajit bearing material is described in WO2017172151A1 and U.S. Patent Application Publication No. 2016/0213713, which are incorporated by reference in its entirety. This pitch may be found in stones, which can be found in proximity to mountain slopes facing the sun with proximity of vegetation within one to five (1-5) kilometers. Such stones or formations can be found in the mountain crevices, caves, and the raw resin deposits sometimes may have an appearance of dark gooey matter oozing out of rocks. Visually the raw resin deposits may appear as a part of the crevice, but if extracted, may be 1 to up to 150 cm in depth, and may be mixed with surrounding rock, sand, pebble, residuals of local plants.

Measuring the identified raw material may be done with simple measuring tape or a ruler. To measure the depth of how deep the deposit in the stones are in a crevice or a rock, a measuring rod with a scale may be used, which allows to identify the depth of the stone. The color of the raw material can range from very dark brown, to red, yellow and shades of white. The presence of white indicates that microorganisms beneficial to the raw material will be properly populated and have processed the matter. Such microorganisms include simple yeasts and aerobic bacteria, which creates multiple metabolites that give the resin its health properties.

In order to determine if the raw material is suitable, it may be tested in the field. In some aspects, the material may be tested for the presence of glycine prior to collection. In some aspects, the material may be tested for the presence of above a threshold amount of glycine (e.g., at least 0.1%, at least 1%, at least 3, at least 5%, at least 10%, at least 15%, at least 25% or even more glycine). In order to be suitable for collection, the material will preferably contain some glycine. Once the raw material is identified the exterior layer may be grated off (e.g., an exterior layer having a depth of between 0.1-10 cm, between 0.1-7 cm, between 0.1-5 cm, between 1-5 cm, between 1-3 cm), and a selected amount of raw material may be taken for testing. The collected raw material may be mixed in predetermined quantities with water and triketohydrindene monohydrate or other reagent suitable for testing for presence of glycine. In some contemplated aspects, a preferred ratio for testing the raw material is one part raw material to one part monohydrate to eight parts water. The mixture may be boiled and then cooled down (e.g., boiled for 5-30 min and cooled down for 5-30 min). Once fully settled, the solution generally has a color ranging from blue to purple. The ideal raw material has a color in the blue violet range, which is indicative of a good amount of glycine being present. This basic initial test suffices for identification of glycine in the raw material amino acids. Later, once the material has been harvested and processed, the presence of Glycine may be reconfirmed with more accurate quantitative and qualitative methods which include High-Performance Liquid Chromatography (HPLC) or infrared (IR) spectrography or any conventional United States Pharmacopeial Convention (USP) accepted method. It may be at this stage that the raw material is deemed suitable for collection and further processing. The raw material is simply picked by hand or extracted with pickaxes or any firm objects that may separate it from the rock, stone or location.

Once the raw material is identified, the external layer(s) containing impurities may be removed with a sharp object like a chisel or a grater or any object with similar or identical functions. The external layer of the raw material may be removed "grated" off to the depth ranging from 1 up to several (e.g., 3, 5, 8, or even more) centimeters. The depth of external layer removal can be measured with a simple ruler or any device that resembles a ruler. Once the external layers are removed the material may be washed or placed into food grade alcohol.

The positive identification of a desired precious metal (gold, platinum, or silver), which could be performed at any point (e.g., before, during or after testing for the presence of glycine), and the positive identification of a suitable amount of glycine is a combination desired for the raw material to manufacture the resin with high content of gold, platinum, or silver. However, it should be appreciated that some contemplated methods do not require that the raw material contain any precious metals.

Once collected the raw resin material may be placed in a thermo-electric cooler, which maintains internal temperatures lower than 48 degrees Celsius. Additionally or alternatively the material may be placed into a container or vessel made at least in part of a precious metal that contacts the material. The coolers with the material may be transported to a facility where the air is continuously purified of environmental pollutants, airborne microbes, dust particles, aerosol particles, and any chemical vapors. In this controlled manufacturing environment, or clean room, the air at any time adjacent to the resin may have minimal or no particles in the air. This may be achieved through controlled enclosures and proper air filtration. The temperature of one or more of the manufacturing space, the vessel, tank or other device in which the resin is being processed, and the resin may advantageously be kept at or under 48 degrees Celsius, or even under 39 degrees Celsius at all times.

The material may be removed from the thermo-controlled or other containers in an air and temperature controlled environment as described above, also called a clean room. Once removed from the containers the raw resin material may be briefly washed off or immersed in up to 99% percent pure $CH_3CH_2OH$ (ethanol) in possible combination with $H20$, or in another suitable solution or liquid.

Further dissolution and filtering of the previously qualified material may take place. The material may be dissolved in preliminary treated water. In order to dissolve the material containing the raw resin, it may be agitated. Such water is generally considered sterile and contains less than 0.25 USP Endotoxin unit per ml with any microscopically detectable particles absent. Initially the water may contain under 10 ppm, under 5 ppm, under 1 ppm, under 0.1 ppm of dissolved solids, or even less. The material may be combined with water in proportions necessary to turn the combination into a free flowing liquid.

Different types of water can be used depending on the type of processed resin which is desired. Minerals, herbal extracts and biologically active substances may be added to the water. The water used may be from sources from specific locations which were previously global positioning system (GPS) identified, the water can be passed through a magnetic field of 1 to 20000 Gauss, or exposed to sound frequencies from 0.1 to 10,000 HZ (e.g., 5 Hz, 7.83 Hz, 3-25 Hz, 3-50 Hz, 432 Hz, 528 Hz, 80-900 Hz, 2,000-2,200 Hz). The material and water may be present in any suitable ratio. The raw resin material may further be dissolved by letting it dissolve passively or agitating it mechanically with any immersed tool that moves at speeds of, for example, less or equal to 0.1 rpm.

Next the solution may be filtered through multiple size filters, as a general rule from higher pore size to smaller pores size. Filters will range from several millimeters down to several microns. This procedure eliminates undesired pebble, sand, sediment, fiber, and large particles. Eventually the solution will pass passively or under pressure through a filter with a pore size equal or possible even less than 0.03 microns. This allows for the filtrate to come out that later will result into manufacturing of highly bioavailable resin, with particles eliminated, which cannot be easily absorbed by the human body. This procedure requires pressure in order to properly filter out the particles not desired due to the lack of bioavailability and manage the production time for the resin. The pressure may be produced either mechanically by a piston or similar device, or gas such as compressed air. Pressure in such case may be sufficient to effectively push the solution through the numerous filter, the pressure being equal (passive) or above 1 psi and up to 14.7 psi or even higher if the technical capability permits. The process may be repeated multiple times.

At any stage before, during or after the filtration process, herbal extracts or minerals can be added to the solution in any form, as could gold, silver, platinum or other precious metals in any form. The extract may be of any plant that is beneficial to human health. The extract could also be a mineral beneficial to human health. Due to the fact that the resin improves effect of herbs on the body is it beneficial to combine the resin and the herbal extracts. Extracts can be received through different processes, the can be introduced in form of liquid, solid and semisolid extracts to the resin. It is important that the extracts are clearly identified for active ingredients and their levels of actives. This is done separately through any conventionally recognized process described in USP or any other pharmacopeia monographs or technical literature. Such extracts may be received either through simple extraction of liquids, oils, or resins of the herb or through any recognized process such as infusion, decoctions, maceration, digestion, expression, percolation, enfleurage, oil expression, steam distillation, solvent extraction, fractional distillation, phytonic extraction, microorganism and gas type of extractions. Minerals also obtained through any conventional and described in USP or any other process or pharmacopeia or technical process may be added. The material may be filtered from 2 to 50 times in order to remove all of the impurities.

After the final stage of filtration the actual resin may be made through removal of moisture from the filtrate. The solution is churned or left idle during the process with or without the occasional churning. Material may be further processed through a high pressure homogenizer, a high speed mixer or alternative process which results in high uniformity and minimal particulate size of 1-10 nm within the particulate within the resulting material. The vessel with the solution may be actively (by contact) or passively (leaving by a heat source) heated to allow the moisture to escape from the solutions and concentrate it to a solid or a semisolid. In order to speed up the removal of moisture one may introduce an air flow from any source and ensure that the moisture can escape from the filtrate into the air or a special space. Another method to remove the excess moisture is via a vacuum. The vessel with resin may be placed a vacuum chamber, the vessel may be heating, and the resin may be slowly churned or mechanically agitated, causing the moisture to escape leaving the resin. Moisture can be measured at any time with a basic moisture meter equipped with a moisture sensor methods that can be used are gravimetric, coulometric, microwave resonance, Karl Fischer, infrared, conductive. The final resin may have a moisture level of between 1 and 25 percent.

As noted above, one or more precious metals in pure, combined, colloidal or ionic form, in water, or in any other form could be added to the material at any stage (or during multiple stages).

At any manufacturing stage, raw material may be in contact with precious metals and be agitated by: movement, predetermined sound frequency (e.g., 1-100,000 Hz), predetermined magnetic frequency (e.g., 1-20,000 Gauss), predetermined light frequency (e.g., 1,000-10,000 Angstroms), predetermined electric frequency (e.g., 0.01-100 Volts) to facilitate transfer of precious metal into the raw material.

At any manufacturing stage raw material can be combined with additional form of gold, platinum, silver, or a combination thereof, to increase content of the precious metal in the resulting product.

The vessels, tools, filters for processing or containing raw material throughout the manufacturing process are preferably made partially or complete of gold, platinum, silver, or other desirable metal. It is contemplated that the raw material will at some or all stages of collecting, processing and packaging may be contained in or agitated with tools, vessels, etc. having a high gold, platinum or silver content. For example, the surfaces that contact the raw material may be made up of between 10-100%, 25-100%, 25-75%, or 50-100% gold, platinum, silver, or a combination thereof.

The resulting product will have genuine shilajit resin with additional benefits from a combination with a bioavailable gold, platinum, silver, or combination thereof. The content and amount of the precious metal in the mineral pitch (shilajit) for consumption by a mammal may be in an amount above 0.01 ppm, preferably above 1 ppm, and in a form which is bioavailable. The content of gold, platinum, or silver will be in the range amount above 0.01 ppm into higher 100,000 ppm and above, possibly between 1-100 ppm, 0.1-100 ppm, 0.01-100 ppm, or 5-5,000 ppm in some embodiments.

The resulting processed resin will be a high quality and pure mineral pitch, with very low levels of undesired impurities. It should be appreciated that gold, silver, platinum, or added or desirable herbal extracts, minerals, are not considered undesired impurities. This level of undesirable contaminants is lower than majority of traditionally manufactured shilajit, mumie or any form of mineral pitch. The processed resin will also have a higher efficacy due to higher bioavailability due to very small size of the resin forming particles. The resin may be tested for the levels of residual or absence of the contaminant levels, microbiological safety, moisture levels by mass ashes not soluble in 10% HCl acid, ashless humic acids and glycine. It is tested by using USP testing procedures or other Pharmacopeia method.

Resulting resin resulting from a properly conducted manufacturing process will have indicator equal or better than the following:

For Lead: 3 mg/kg
For Arsenic: 6 mg/kg
For Cadmium: 0.5 mg/kg
For mercury: 1 mg/kg
For microbiological pathogens: less than 10 GFU/g
Moisture Levels by mass: 0.001 up to 60%
Ashes not soluble in 10 HCl: not exceeding 1.6%
Ashless humic acids: no less than 5%
Glycine: no less than 1%

Once the resulting solid or semisolid resin passes or is better than the above stated criteria. It can be repackaged in of either transportation or individual distribution. For transportation the resin may be packaged in containers that are completely opaque to light. In such state with no penetration of light the resin is in a "dormant" state and will indefinitely store and can be transported for an indefinitely long time. (wholesale packaging first phase)

The second method of packaging may be in the biophotonic glass. Biophotonics improves the properties of nutritives and will substantially improve the quality of the resin. Such glass with allow the permeation of the spectrum of light within the wavelength of 315 to 450 nm, and frequency of the 668-789 THz, it also blocks the light in the spectrum of 450 to 620 nm, and allows the light through in the range of 620 to 750 nm. At this point the resin can be stored indefinitely and will be stable over indefinite period of time.

The resin may be made into or left as a liquid, semi-solid of various consistency, solid, powder to be used independently or as an ingredient in formulations.

After reading this description it will become apparent to one skilled in the art how to implement the invention in various alternative embodiments and alternative applications. However, all the various embodiments of the present invention will not be described herein. It is understood that the embodiments presented here are presented by way of an example only, and not limitation. As such, this detailed description of various alternative embodiments should not be construed to limit the scope or breadth of the present invention as set forth below.

With reference to FIG. 1, a flow diagram showing contemplated steps of a method for identifying, collecting and processing raw mineral resin is shown. As illustrated, the first step is to identify the raw material or shilajit bearing material or stone at step 10.

Once the raw material is identified the next step in the process of FIG. 1 is to collect a small portion of the resin and test it in the field, step 20. In some aspects, if the tests determine that the material contains glycine and a precious metal, it will be suitable for collection. In some aspects, if the tests determine that the material contains glycine, it will be suitable for collection.

Once the material has been tested and has been confirmed to contain glycine and optionally precious metal content, it is collected, step 30. The next step in the process of FIG. 1 is the transport of the material at step 40.

At step 50 the material is held in the clean room until it is further processed. At step 60 the processing of the raw material commences and takes place in the clean room. At this stage the raw material is removed from the thermo-controlled containers. Once the material is removed from the containers the raw resin material may be briefly washed of or immersed in up to a 99% pure ethanol in combination with water (H20).

Figure 2:
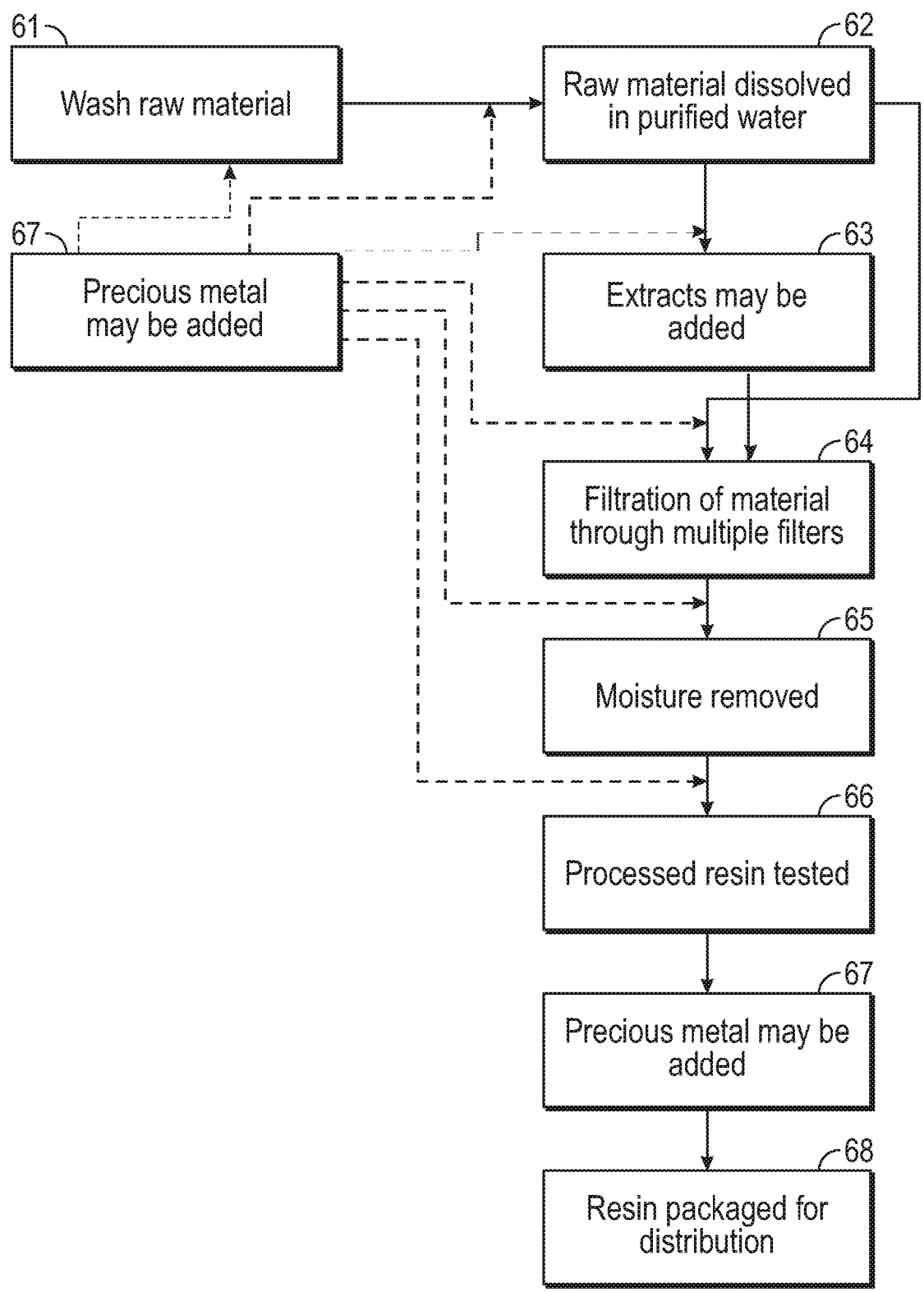
FIG. 2 is a flow diagram which shows an exemplary multi-step processing of raw resin to processed resin.

Referring to FIG. 2, a multi-step processing of the raw material commences so that the raw material may be formed into processed material for distribution for human consumption. As shown in the Figure in step 67, it is contemplated that one or more precious metals could be added to the material at any stage, including at multiple stages, during the processing of the material. It should also be appreciated that one or more precious metals could be added to the raw material during the collection and prior to processing of the raw material, or during the packaging stage post-processing of the material.

The raw material is first washed off as set forth above, step 61. Next the raw material may be dissolved in preliminarily treated water at step 62. The water in which the resin is dissolved may be sterile and contains less than 0.25 USP endotoxin unit per ml with any microscopically detectable particles absent. The material may be combined with the water in proportions necessary to turn the combination in to a free flowing liquid. In order to dissolve the raw material in the water it should be agitated. Depending on the consistency of the raw material this agitation can vary in length and frequency. Gold, silver, platinum, a combination thereof, or any other suitable precious metal may be added to the material when the material is combined with a liquid (e.g., when dissolved in purified water, step 62). The precious metal(s) could additionally or alternatively be added at one, two, three, or more points during the processing of the material until packaged as shown in FIG. 2.

Once the material has been dissolved it will be filtered at step 64. However if desired extracts may be added to the raw material at step 63 (or possibly at one or more other stages during processing). For example, herbal extracts or minerals can be added to the solution during the washing stage 61 or dissolving stage 62, or could be added later at stages, e.g., steps 64 or 65.

At another stage of processing step 64 the raw material dissolved in purified water, either with or without extracts, is filtered between 2 to 50 times to remove impurities.

After the filtration process at step 64 is complete the moisture is removed at step 65. Once the moisture has been released from the resin it will be a semi-solid or paste and is tested to determine its moisture level. The moisture sensor methods that can be used are gravimetric, coulometric, microwave resonance, Karl Fischer, infrared, conductive. The final resin should have a moisture level of between 1 and 25% of the mass of the product.

Once the moisture is removed at step 65 the processed resin is then tested for the criteria set forth above (e.g., lead and glycine content), at step 66. Once the resulting solid or semi-solid processed resin passes or is better than the criteria set forth above, or at any other time during the collection, containment or processing of the material, an optional step of adding additional gold or other precious metal to the material is provided to increase the final precious metal content as shown in step 67.

The resin may be used in its current state or may be made into a liquid, a semi-solid of various consistency, a solid or a powder for human consumption.

Finally, the resin will be packaged for distribution at step 68 (e.g., as a liquid, a semi-solid, a solid, a powder). Once the resin is packaged it is ready to be distributed for sale to the public and for human consumption.

Thus, specific embodiments and applications of methods of mineral pitch resin with precious metal content for human consumption have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

As used in the description herein and throughout the claims that follow, the meaning of "a," "an," and "the" includes plural reference unless the context clearly dictates otherwise.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

What is claimed is:

1. A mineral pitch resin product in the form of a semisolid, solid, liquid or powder consisting of a pure form of at least one of gold, platinum and silver present in an amount above 1 ppm and below 100 ppm, and wherein the mineral pitch resin product has a mercury concentration that does not exceed 1 mg/kg, an arsenic concentration that does not exceed 6 mg/kg, and a glycine concentration of no less than 1%.

2. The product of claim 1, wherein the at least one of gold, platinum and silver is present in an amount above 50 ppm.

3. The product of claim 1, wherein the product is orally bioavailable.

4. The product of claim 1, wherein the product is safe and for consumption by mammals and plants.

5. The product of claim 1, wherein the at least one of gold, platinum and silver is present in an amount effective to improve joint and bone health.

6. The product of claim 1, wherein the at least one of gold, platinum and silver is present in an amount effective to improve at least one of immune health and natural organism defenses.

7. The product of claim 1, wherein the at least one of gold, platinum and silver is present in an amount effective to improve metabolism.

8. The product of claim 1, wherein the at least one of gold, platinum and silver is present in an amount effective to improve brain health and intelligent quotient.

9. A method of producing the mineral pitch resin product of claim 1, the method comprising:

dissolving collected raw mineral pitch to create a solution;
filtering the solution with one or more filters which eliminate particles;
mixing the filtered solution and dehumidifying and de-moisturizing it so that it turns into a resin or paste form;
contacting the resin or paste form of raw mineral pitch material with a device including at least one of gold, platinum and silver.

10. The method of claim 9, further comprising combining the raw mineral pitch material with at least one of gold, platinum, and silver to form the mineral pitch resin product.

11. The method of claim 9, further comprising agitating the raw mineral pitch material with at least one of a predetermined sound frequency, a predetermined electric frequency, and a predetermined light frequency.

12. The method of claim 9, further comprising storing the product in a container having an inner surface made at least in part of at least one of gold, platinum, and silver.

13. The method of claim 9, wherein the device further includes water.

14. The product of claim 1, wherein the product is in the form of a semisolid, solid, or liquid.

15. A mineral pitch resin product in the form of a semisolid, solid, liquid or powder comprising a pure form of platinum present in an amount above 1 ppm and below 100 ppm, and wherein the mineral pitch resin product has a mercury concentration that does not exceed 1 mg/kg, an arsenic concentration that does not exceed 6 mg/kg, and a glycine concentration of no less than 1%.

16. A mineral pitch resin product in the form of a semisolid, solid, or liquid comprising a pure form of at least one of gold, platinum and silver present in an amount above 1 ppm and below 100 ppm, and wherein the mineral pitch resin product has a mercury concentration that does not exceed 1 mg/kg, an arsenic concentration that does not exceed 6 mg/kg, and a glycine concentration of no less than 1%.

* * * * *